(12) United States Patent
Gen

(10) Patent No.: US 6,897,245 B2
(45) Date of Patent: May 24, 2005

(54) MEDICAL MATERIALS STERILIZED BY RADIATION AND THEIR WAYS IN USE

(75) Inventor: Shokyu Gen, Kyoto (JP)

(73) Assignee: BMG Incorporated, Kyoto (JP)

( * ) Notice: Subject to any disclaimer, the term of this patent is extended or adjusted under 35 U.S.C. 154(b) by 329 days.

(21) Appl. No.: 10/135,122

(22) Filed: Apr. 30, 2002

(65) Prior Publication Data

US 2002/0197296 A1 Dec. 26, 2002

(30) Foreign Application Priority Data

Jun. 21, 2001 (JP) ........................................ 2001-228719

(51) Int. Cl.⁷ .............................................. A61K 47/30
(52) U.S. Cl. ................................................. 514/772.3
(58) Field of Search ...................................... 514/772.3

(56) References Cited

U.S. PATENT DOCUMENTS 5,998,551 A   12/1999   O'Neil et al.

FOREIGN PATENT DOCUMENTS

| JP | 2000273233 | * 10/2000 |
|---|---|---|
| JP | 2001-072851 | 3/2001 |
| WO | WO 98/15199 | 4/1998 |

* cited by examiner

*Primary Examiner*—Carlos A. Azpuru
(74) *Attorney, Agent, or Firm*—Jordan and Hamburg LLP

(57) ABSTRACT

Present invention provides medical material sterilized by radioisotope, comprising polymer composite using in living body, containing multifunctional triazine compounds at weight ratio range of 0.01 to 20 weight percent to the polymer.

The present invention shows the fabrication of polymer composite having good heat and radiation resistance, by preventing heat molding record and irradiation on sterilized processes from deteriorating molecular weight caused on heat and radiation decomposition of the polymer. It is possible that the polymer composite is applied for the medical field of decomposable and bio-absorbable polymers and even bio-nonabsorbent polymers such as suture of operation or bonding agent for broken bone as a result. Furthermore, it is possible that the polymer composite is applied for not only medical material but also food wrapping material of industrial use.

4 Claims, No Drawings

MEDICAL MATERIALS STERILIZED BY RADIATION AND THEIR WAYS IN USE

BACKGROUND OF THE INVENTION

1. Field of the Invention

Present invention relates to medical polymer materials sterilized by radiation and their use, particularly to medical polymer materials showing small deterioration or decomposition over time passage after being exposed to radiation such as γ ray or a microwave.

2. Description of the Related Art

There are many kinds of materials employed in medical use, while more functional materials are expected to be employed in medical field, notwithstanding; and metals, ceramics and polymers are pointed out as biomaterials. Required properties of the medical material include sterilization capability in product stage as important factor, in addition to desirable functions of medical material.

Sterilization is defined in Japan Pharmacopoeia as sterilizing or removing all microbes in materials. There are pointed out 12 sterilization methods of 5 groups in Japan Pharmacopoeia, among which, sterilization methods by high pressure vapor, ethylene oxide gas (EOG) and radiation are widely and generally employed for use in living body.

Sterilization condition of high pressure vapor is applied for about 20 minutes at 121° C. of 1.0 kg/cm$^2$G of saturated vapor pressure in relative simple autoclave. Such condition is possible to be employed in sterilization of many kinds of medical materials that stand high pressure and temperature. However such sterilization methods are employed in almost no case of organic polymer materials, because of causing deterioration or decomposition, while many kinds of metals and ceramics are able to stand high pressure and temperature.

On the other hand, speaking to EOG steralization method, sterilization instruments are developed in order to improve effectiveness, efficiency and safety in sterilization, because EOG is known as effective as a disinfectant. This sterilization method seems best in comparison with others in order to prevent deterioration of the raw materials. However EOG sterilization method recently come to be avoided in employing, because it is pointed out that EOG remains in medical materials after sterilization, and has bad effect on living body. According to recent research, sterilization method employed in suture for operation, disposable surgical gown and a hypodermic syringe, comes to be changed from usual EOG to radiation sterilization methods, because of high toxicity of residual EOG and complicated procedure for packing.

Radiation sterilization method is taken attention as other sterilization method, in which used are radial rays that are such beam of particles inclusive of light, coming from radioactive disintegration or the like, including α, β, γ rays, and neutron and X ray. Generally applied for the sterilization of medical polymer material are known to be γ ray coming from $^{60}$Co and electron beams.

As γ and electron beams have no serious damage to general-purpose polymer materials such as polyethylene, polypropylene, polyethylene chloride, polystyrene and synthetic rubbers, those polymers are possible to be sterilized by radiation and have been widely used.

However, it is pointed out that coloration, bad smells and oxidation degradation, happen to occur on passage of time, and are caused on generally employed sterilization irradiation amount of about 25 kGy. Thus, new sterilization methods such as plasma and ultra-violet methods are developing. The plasma and ultra-violet methods are partly applied as a simple and easy method, but has a very narrow application because of permeability.

Radiation exposure effects on the polymer materials are distinguished by cross-linking and collapse of the polymer chains, which are independent on irradiation rate, but proportional to irradiated dose over wide range. Cross-linking is defined as follows; radicals are generated by irradiation process, in which new inter- and intramolecular connections are generated on polymer molecules, molecular weight of the polymer finally increases to infinity, and the cross-linked polymer is insoluble in all kinds of solvents. On the other hand, the collapse of the polymer is defined as follows; polymers happen to deteriorate their molecular weight and mechanical properties, because the polymer chains are cut by irradiation.

The polymers are classified into cross-linking and collapsing type polymers dependent on radiation effect. Typical examples of cross-linking polymer are polyethylene, polypropylene, nylon, polystyrene, polyester, natural rubber and silicon resin. On the other hand, collapsing type polymers include poly-methylmethacrylate, Teflon (registered trademark), poly-isobutylene, collagen, cellulose and bio-decomposable polymers such as poly-lactic acid. However, even cross-linking type polymers happen inevitably to deteriorate in mechanical properties similar to the collapsing type ones because the polymer chains are cut by irradiation and generated radicals. Therefore, even polyethylene, which is easiest in cross-linking by radiation, happens to deteriorate in mechanical properties by time passage after irradiation. It is because radicals generated by irradiation do not extinct in short time, but remain in the polymer material for long time as free radicals and cause cutting of polymer chain by reacting with oxygen by passage of time.

The polymers are heat-treated at a temperature higher than 100° C. in order to remove the free radicals. However, when the polymers are heat-treated for several hours at a temperature higher than 100° C. in order to prepare cup and plate for artificial hip and knee joints made from ultra high molecular weight poly ethylene (UHMWPE), there is fear of deforming of the product by remained strain.

Many polymer materials made of polypropylene and sterilized by radiation are available for disposable medical materials such as suture for operation, hypodermic syringe, filter, surgical gown, and non-woven sheet. It is proposed the methods of compounding the propylene with hydrated rosin-methyl-ester (JP61-213243A) or styrene resin (JP-07-157922A) in order to prevent deterioration and bad smell arisen from sterilizing by radiation. However, it is not quite effective because the free radicals cannot completely be removed from by the above additives.

Only several kinds of polymers including polypropylene and polyethylene are suitable for sterilizing by radiation among many cross-linking types of decomposable and bio-absorbable polymers. Reason why radiation sterilization method is not employed in even radiation cross-linking type polymers of nylon or poly-vinylidene fluoride, is because the polymers happen to partly cross-link each other and partly decompose at same time, generate oligomers and monomers, and may cause toxicity. Furthermore, we cannot employ the radiation sterilization method on the suture for surgical operation, because the suture requires mechanical properties as maintained in long time and because of toxicity problem. Recently, notwithstanding that poly methyl methacrylate and silicon resin are generally employed on contact lenses and ocular lenses in accordance with their excellent optical properties and biological compatibility, EOG sterilization is inevitable in end product because radiation is hazardous for these polymers. It is problem that EOG remains in medical materials after sterilization. As eye is the most sensitive organ in comparison with other organs and tissues, it is all the more worrisome to give bad effect on living body.

On the other hand, medical polymer materials for implantation recently include suture for operation made from decomposable and bio-absorbable polymer, artificial dura mater, bonding agent for broken bone; and it is expected to grow in various uses. In spite of a fact that it passed more than 30 years since the suture for operation made from decomposable and bio-absorbable polymer was applied in clinic, EOG sterilization method is still employed. It is because the decomposable and bio-absorbable polymer is by nature composed of chemical structure that is unstable in heat, light, radiation and moisture.

Sterilization methods by high pressure vapor of EOG and radiation are widely and generally employed as mentioned above. Targets of present invention are to solve the following problems of radiation sterization method.

(1) Prevention of medical material deterioration caused on irradiation.
(2) Expansion of way of use of radiation steralization method to medical materials that have been impossible to be employed in past.

Moreover, if it is possible to sterilize non-decomposable and non-bio-absorbable polymer by radiation, advantageous effect is immense. Especially, if it is possible to apply radiation sterilization method for decomposable and bio absorbable polymer for medical use that have been impossible to be applied with radiation sterilization in past, we cannot guess the usefulness in social and economical scopes.

SUMMARY OF THE INVENTION

Present invention provides medical material sterilized by radiation for use in living body, containing a polymer and a multifunctional triazine compound at a weight ratio in a range of 0.01 to 20 weight percent to the polymer.

The present invention provides polymer materials having good heat and radiation resistance, by curbing heat history during molding and thermolysis and radiolysis during radiation sterilization. Consequently, the radiation sterilization becomes applicable to the biodegradable and bioabsorbable materials for medical use as well as the non-biodegradable and non-bioabsorbable materials for medical use, and thus applicable to sutures for surgery or bonding agent for broken bone for examples. Furthermore, the radiation sterilization becomes applicable not only for medical use but also for industrial use such as food wrapping.

DETAILED DESCRIPTION OF THE INVENTION

The inventor of the present invention has found followings, after wholeheartedly researching above subject: for all kinds of polymer materials and even for ones having seemed as impossible to be irradiated; inclusion of triallyl isocyanurate compound, which is one of multi-functional triazine group compounds, prevents the polymer from cutting, decomposing their chains and forming cross linkage between polymer chains, and prevents generation of bad smells and deterioration of mechanical properties irradiation. The polymers according to the present invention are selected from both the biodegradable and bio-absorbable polymer materials and the non-biodegradable and non-bioabsorbable polymer materials.

Medical materials of the biodegradable and bio-absorbable polymer materials according to the present invention, include; natural polymers selected from collagen, gelatin, chitin, chitosan, silk, cellulose, hyaluronic acid, microbe-produced polyester such as poly β-hydroxybutylate, albumin and dextrin, and the biodegradable and bio-absorbable synthetic polymers selected from poly-glutamine, poly glycolic acid, poly-lactic acid, poly caprolactone, poly dioxanone, tri-methylene carbonate, and their co polymers such as glycolic acid-caprolactone copolymer, lactic acid-caprolactone copolymer, lactic acid-dioxanone copolymer, glycolic acid-tri-methylene carbonate copolymer, as well as poly peptide, polyphosphatase, poly butylene succinate and their blends.

On the other hand, medical materials of the non-biodegradable and non-bioabsorbable polymers are selected from poly propylene, poly ethylene, poly amide, poly ester, poly carbonate, poly fluorovinylidene, silicon, poly urethane, natural rubber, synthetic rubber, poly vinylchloride, poly acetal, poly styrene, styrene resin, poly acrylonitrile, poly tetra-fluoro-ethylene, ethylene-vinyl-alcohol copolymer, ethylene-vinyl acetate copolymer, poly methyl methacrylate, poly hydroxyethyl methacrylate, and poly sulphone, as well as their blends.

Cross-linking agent of the polymer applied in present invention is the multi-functional triazine compound. Triallyl isocyanurate, triallyl metha-isocyanurate, triallyl (2,3 di bromo) iso cyanurate are included in the triazine compound and triallyl isocyanurate is preferred based on its nature of reactive monomer.

The triazine compound is added by 0.01 to 20 weight percent, preferably 0.1 to 10 weight percent to the polymer before molding of the polymer material. It is preferred to fabricate uniform product by adding the triazine compound before the molding.

Cross-linking between polymer chains is achieved by irradiation of 10 to 50 kGy at final producing stage after molding. Deterioration starts with higher than 50 kGy irradiation, and sterilization effect is in shortage at lower than 10 kGy irradiation.

Furthermore, it is possible to blend the polymer with known heat stabilizer, antioxidant, ultraviolet absorbent, light stabilizer, colorant, antistatic, lubricant, nucleating agent, fire retardant, or filler within limit of not spoiling effect of the present invention. For example, it is effective to blend the polymer and antioxidant such as vitamin E or catechin.

Medical material according to the present invention is the ways in use, employing on suture for operation, artificial blood vessel, bonding agent for broken bone, dental material, wound protector, artificial skin, contact lenses, ocular lenses, artificial ligament, artificial valve, artificial joint scraping parts, mesh, medical non-woven fabric, stent, clip, Hotchkiss, artificial dura mater, scaffold in tissue regeneration, provender from adhesion, anatomosis splint, disposable hypodermic syringe, catheter, blood bag and tube for infusion, disposable surgical gown and glove, sheet and filter.

The medical materials of the present invention are possible to be applied for not only in medical uses, but also in industrial uses including packing or wrapping. It is possible to improve mechanical properties and bio-decomposability by conducting irradiation for sterilization and cross-linking between polymer chains at final producing stage after molding of the products in the industrial uses.

EXAMPLE

We explain details of the present invention by way of following examples, however, not restricting the scope of the invention by the explanation. Test procedure of the tensile strength and elongation was performed according to prescription of JIS L 1017. We have examined the specimen by employing tensile-tester of "Shimazu Autogragh 100 type", in a room maintained at constant temperature of 25° C., humidity of 65 RH %, with specimen length of 250 mm and test speed of 300 mm/min.

Example 1

Pellets of polypropylene having weight-average molecular weight of about 320,000, were added with triallyl cyanurate by 2.0 weight percent, and then were subjected to melt-spinning by simple type spinner and drawing 4 times by warm-air-circulating type stretching machine. Produced polypropylene fiber was packed in an Aluminum/Polyethylene laminated bag replaced by nitrogen gas, and then irradiated with electron rays of 25 kGy.

Irradiated fiber showed properties of being non-soluble but swelling in heated xylene, and gelation ratio of about 0.75, caused by having cross-linking structure. And, tensile strength and elongation at break of the fiber before and after irradiation, were 5.7 g/d and 31%, and 6.1 g/d and 29%, respectively.

Comparative Example 1

The polypropylen pellets were melt-spun by the simple type spinner, same to example 1, but not added with the triallyl cyanurate, and then subjected to the drawing 4 times by the warm-air-circulating type stretching machine. Produced polypropylene fiber was packed in an Aluminum/Polyethylene laminated bag replaced by nitrogen gas, and then irradiated with electron ray of 25 kGy.

Irradiated fiber showed properties of soluble in heated xylene, and gelation ratio of about 0 percent. And, tensile strength and elongation at break of the fiber after irradiation, were 3.2 g/d and 21%.

Example 2

Pellets of poly vinylidene fluoride having weight-average molecular weight of about 680,000, were added with triallyl cyanurate by 1.0 weight percent, and then subjected to melt-spinning by the simple type spinner and drawing 5 times in a bath at 150° C. Produced poly vinylidene fluoride fiber was packed in an Aluminum/Polyethylene laminated bag under decompressed pressure, and then irradiated with Co60 γ rays of 25 kGy.

Irradiated fiber showed properties of being non-soluble but swelling in dimethyl formamide, and gelation ratio of about 0.68, caused by having cross-linking structure. And, tensile strength and elongation at break of the fiber before and after irradiation, were 5.8 g/d and 27%, and 6.2 g/d and 25%, respectively.

Comparative Example 2

The poly vinylidene fluoride pellets were melt-spun by the simple type spinner, same to example 2, but not added with the triallyl cyanurate, and then subjected to the drawing by the warm-air-circulating stretching machine. Produced polypropylene fiber was packed in an Aluminum/Polyethylene laminated bag under decompressed pressure, and then irradiated with Co60 γ rays s of 25 kGy.

Irradiated fiber showed properties of being soluble in heated dimethyl formamide, and gelation ratio of several percents. And, tensile strength and elongation at break of the fiber after γ ray irradiation, were 3.9 g/d and 20%.

Example 3

Pellets of dried nylon 6 having weight-average molecular weight of about 55,000, were added with triallyl cyanurate by 0.8 weight percent, and then subjected to melt-spinning by simple type spinner and drawing of 4 times by sandwiching between a pair of heated rollers. Produced nylon 6 fiber was packed in an Aluminum/Polyethylene laminated bag replaced by nitrogen gas, and then irradiated with electron rays of 25 kGy.

Irradiated fiber showed properties of being non-soluble but swelling in heated m-cresol, and gelation ratio of about 0.66. And, tensile strength and elongation at break of the fiber before and after irradiation, were 6.3 g/d and 29%, and 6.8 g/d and 27%, respectively.

Comparative Example 3

The nylon 6 pellets were melt-spun by the simple type spinner, same to example 3, but not added with the triallyl cyanurate and then subjected to the drawing. Produced nylon 6 fiber was packed in an Aluminum/Polyethylene laminated bag under decompressed pressure, and then irradiated with electron rays.

Irradiated fiber showed properties of being soluble in heated m-cresol, and gelation ratio of 0 percent. And, tensile strength and elongation at break of the fiber after electron rays irradiation, were 5.2 g/d and 23%.

Example 4 and Comparative Example 4

Pellets of dried poly methyl methacrylate having weight-average molecular weight of about 120,000, were added with triallyl cyanurate by 2.0 weight percent, and then molded to a column of 20 mm diameter and 10 cm length by injection molder. After cutting the column to shape of ocular lenses, produced poly methylmethacrylate lenses were packed in an Aluminum/Polyethylene laminated bag replaced by nitrogen gas, and then irradiated with Co60 gamma ray of 25 kGy.

Irradiated specimen showed properties of being non-soluble but swelling in tetrahydrofuran, and gelation ratio of about 0.70. On the contrary, vacuum-packed specimen (comparative example 4) that was formed and cut from an injection molded column that is not added with the triallyl cyanurate, and then irradiated with Co60 γ rays of 25 kGy, was happened to turn yellow and have bad smell caused by the decomposition; and the polymer was deteriorated to show the weight-average molecular weight of about 80,000.

Example 5

Dried poly dioxanone (in Hexa-fluoro iso propanol or HFIP) solution composed of a polymer having intrinsic viscosity of 2.5, was added with triallyl cyanurate by 2.5 weight percent, and then subjected to spinning by the simple type spinner, drawing and annealing, as to give a monofilament fiber. Produced monofilament fiber was packed in an Aluminum/Polyethylene laminated bag replaced by nitrogen gas, and then irradiated with electron rays of 25 kGy.

Irradiated monofimament fiber showed properties of being non-soluble but swelling in heated HFIP, and gelation ratio of about 0.77. And, tensile strength and elongation at break of the fiber before and after irradiation, were 7.7 g/d and 36%, and 4.8 g/d and 35%, respectively.

Comparative Example 5

The poly-dioxaone was melt-spun by the simple type spinner, same to example 5, but not added with the triallyl cyanurate, and then subjected to drawing and annealing. Produced monofilament fiber was packed in an Aluminum/Polyethylene laminated bag under decompressed pressure, and then irradiated with the electron rays.

Irradiated monofilament fiber showed properties of being soluble in HFIP, and gelation ratio of 0 percent. And, tensile strength and at break of the monofilament fiber after electron ray irradiation, were 3.1 g/d and 22%.

Example 6

Pellets of dried poly L lactide L-lactide (PLLA) having weight-average molecular weight of about 340,000, were added with triallyl cyanurate by 1.0 weight percent, and then molded to a rod column of 10 mm diameter and 10 cm length by the injection molder. The rod column was subjected to solid-state hydrostatic extrusion at 140° C. and extrusion ratio of 4. Thus obtained product was packed in an Aluminum/Polyethylene laminated bag replaced by nitrogen gas, and then irradiated with Co60 γ rays of 25 kGy.

Irradiated mold product showed properties of being non-soluble but swelling in methylene chloride and gelation ratio of about 0.67. And, bending strengths of the mold product before and after irradiation, were 250 and 260 MPa, respectively.

Comparative Example 6

The PLLA pellets were molded into a rod column by the injection molder, and then subjected to the solid-state hydrostatic extrusion as same to the example 6, but not added with the triallyl cyanurate. Thus obtained product was packed in an Aluminum/Polyethylene laminated bag and then irradiated with Co60 γ rays of 25 kGy.

Irradiated PLLA product showed properties of being soluble in methylene chloride, and gelation ratio of 0 percents. And, bending strength after gamma ray irradiation was as deteriorated as 180 MPa.

Example 7

Ultra high molecule poly ethylene (UHMWPE) powder composed of a polymer having weight-average molecular weight of about 4,500,000, was added with triallyl cyanurate by 1.0 weight percent, and then molded to a plate of 10 mm thickness by hot-press molder. Produced UHMWPE plate was packed in an Aluminum/Polyethylene laminated bag replaced by nitrogen gas, and then irradiated with Co60 γ rays of 25 kGy.

Irradiated plate showed properties of being non-soluble but swelling in hot tetralin solvent and gelation ratio of about 0.79. And, abrasion resistance index evaluated by pin-on-flat tester before and after irradiation, were $0.9(\times 10^{-10}$ g/Nm) and $0.2(\times 10^{-10}$ g/Nm), respectively. Further, abrasion resistance index of 0.2 was not changed after oxidation test performed at 80° C. in ambient air for one week.

Comparative Example 7

The ultra high molecule poly ethylene (UHMWPE) powder composed of the polymer having weight-average molecular weight of about 4,500,000 was molded to a plate but not added with the triallyl cyanurate. Thus obtained plate was packed in an Aluminum/Polyethylene laminated bag replaced by nitrogen gas, and then irradiated with Co60 γ rays of 25 kGy.

Irradiated plate showed properties of being non-soluble but swelling in hot tetralin solvent and gelation ratio of about 0.58. And, abrasion resistance index evaluated by similar method of example 7, was $0.6(\times 10^{-10}$ g/Nm), however, abrasion resistance index of 14 was increased after oxidation test.

Example 8

Dried pellets of poly glycolic acid which showed intrinsic viscosity η sp/c of 1.4 at 170° C. in a solvent mixture of 10 weight part of phenol and 7 weight part of 2.2.6 tri-chlorophenol, were added with triallyl iso-cyanurate by 1.0 wt. percent, and then subjected to melt spinning by the simple type spinner, drawing, and annealing and subsequently a multifilament yarn being fabricated. Produced multifilament yarn was packed in an Aluminum/Polyethylene laminated bag replaced by nitrogen gas, and then irradiated with electron rays of 25 kGy.

Irradiated multifilament yarn showed properties of being non-soluble but swelling in solvent mixture at 170° C. and gelation ratio of about 0.48. And, tensile strength and elongation at break of the fiber before and after irradiation, were almost same values of 7.2 g/d and 22%. For comparison, dried pellets of the poly glycolic acid added with no triallyl iso-cyanurate were subjected to melt spinning by the simple type spinner, and then packed in an Aluminum/Polyethylene laminated bag. Thus obtained product showed degraded ones of tensile strength and elongation at break, which area 3.8 g/d and 17%.

Example 9

Dried pellets of a copolymer of lactic acid and caprolactone having weight-average molecular weight of about 420,000, were added with triallyl iso-cyanurate by 1.0 wt. percent and with vitamin E by 0.2 wt. percent, and then subjected to melt-spinning by the simple type spinner, drawing, and annealing as to give a monofilament yarn. Produced monofilament yarn was packed in an Aluminum/Polyethylene laminated bag replaced by nitrogen gas, and then irradiated with electron rays of 25 kGy.

Irradiated monofilament yarn showed properties of being non-soluble but swelling in chloroform and gelation ratio of about 0.53. And tensile strength and elongation at break of the fiber before and after irradiation, were almost same values of 5.7 g/d and 36%.

For comparison, dried pellets of the copolymer of lactic acid and caprolactone added with no triallyl iso-cyanurate were subjected to melt-spinning by the simple type spinner, and then packed in an Aluminum/Polyethylene laminated bag. Thus obtained product showed degraded ones of tensile strength and elongation at break, which are 2.9 g/d and 21%.

What we claim is:

1. A method of preparing a sterilized article for medical use in a living body or for use in food wrapping, comprising mixing a polymer and a multifunctional triazine compound as crosslinking agent for the polymer at a weight ratio in a range of 0.1 to 10 weight percent to the polymer;

molding or shaping the polymer into a fiber or yarn, a fabric, a film or sheet, a mesh or filter, a tube, a bag, a glove, a syringe, a lense or other shaped article; and irradiating such molded or shaped article with electron beam or gamma rays under inert atmosphere or under decompressed pressure, in an extent of 10 to 50 kGy.

2. A method of preparing a sterilized article according to claim 1, said polymer being a bio-absorbable and decomposable natural polymer or a bio-absorbable and decomposable synthetic polymer.

3. A method of preparing a sterilized article according to claim 1 or 2, wherein before said irradiating, said molded or shaped article is packed in a bag of laminated film comprised of an aluminum layer and a resin layer, which is replaced with inert gas or decompressed.

4. A method of preparing a sterilized article according to claim 1, wherein other shaped article is selected from a group consisting of: a suture for operation, an artificial blood vessel, bonding agent for broken bone, dental material, wound protector, artificial skin, contact lense, ocular lense, artificial ligament, artificial valve, artificial joint scraping parts, mesh, medical non-woven fabric, stent, clip, Hotchkiss, artificial dura meter, foothold in tissue regeneration, antiadhesive material, anatomosis splint, disposable hypodermic syringe, catheter, blood bag and tube for infusion, disposable surgical gown and glove, disposable surgical sheet and filter.

* * * * *